(12) United States Patent
Nishtala (10) Patent No.: US 8,333,753 B2
(45) Date of Patent: Dec. 18, 2012

(54) DRAINS FOR USE IN MEDICAL APPLICATIONS AND METHODS OF USING THE SAME

(75) Inventor: Vasu Nishtala, Snellville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 971 days.

(21) Appl. No.: 12/160,032

(22) PCT Filed: Jan. 5, 2007

(86) PCT No.: PCT/US2007/060156
§ 371 (c)(1),
(2), (4) Date: Feb. 3, 2009

(87) PCT Pub. No.: WO2007/082157
PCT Pub. Date: Jul. 19, 2007

(65) Prior Publication Data
US 2010/0056988 A1    Mar. 4, 2010

Related U.S. Application Data

(60) Provisional application No. 60/743,103, filed on Jan. 6, 2006.

(51) Int. Cl.
*A61M 27/00* (2006.01)
(52) U.S. Cl. .................................................. 604/541
(58) Field of Classification Search .................. 604/541
See application file for complete search history.

(56) References Cited

U.S. PATENT DOCUMENTS

| | | | | |
|---|---|---|---|---|
| 1,045,326 | A * | 11/1912 | Ruflin | 604/43 |
| 2,460,473 | A * | 2/1949 | Smith | 604/43 |
| 2,498,692 | A * | 2/1950 | Mains | 604/95.04 |
| 4,445,897 | A * | 5/1984 | Ekbladh et al. | 604/541 |
| 4,573,965 | A * | 3/1986 | Russo | 604/30 |
| 4,650,463 | A * | 3/1987 | LeVeen et al. | 604/43 |
| 4,850,351 | A * | 7/1989 | Herman et al. | 606/7 |
| 4,950,232 | A * | 8/1990 | Ruzicka et al. | 604/43 |

(Continued)

FOREIGN PATENT DOCUMENTS

EP    0680353 B1    7/2002

OTHER PUBLICATIONS

Canadian Application No. 2,635,596 filed Jan. 5, 2007 First Examiner's Report dated Apr. 14, 2010.

(Continued)

*Primary Examiner* — Kevin C Sirmons
*Assistant Examiner* — Ginger T Chapman
(74) *Attorney, Agent, or Firm* — Rutan & Tucker, LLP (57) ABSTRACT

A drain for use in medical applications may include an elongated conduit configured to be implanted in a body cavity, wherein the conduit has a proximal end and a distal end. The conduit may include at least one channel configured to drain fluid from the body cavity and at least one lumen extending from the proximal end to the distal end of the conduit. The lumen may be at least partially surrounded by the at least one channel and may be separated from the at least one channel by a wall. At least one hole in the wall may be configured to provide fluid communication between the lumen and the at least one channel.

4 Claims, 5 Drawing Sheets

U.S. PATENT DOCUMENTS

| | | | |
|---|---|---|---|
| 5,116,310 A | | 5/1992 | Seder et al. |
| 5,238,005 A | | 8/1993 | Imran |
| 5,360,414 A | * | 11/1994 | Yarger .......................... 604/264 |
| 5,370,675 A | | 12/1994 | Edwards et al. |
| 6,329,488 B1 | | 12/2001 | Terry et al. |
| 6,596,401 B1 | | 7/2003 | Terry et al. |
| 6,716,895 B1 | | 4/2004 | Terry |
| 6,887,228 B2 | | 5/2005 | McKay |
| 6,893,424 B2 | | 5/2005 | Shchervinsky |
| 6,949,598 B2 | | 9/2005 | Terry |
| 7,125,402 B1 | * | 10/2006 | Yarger .......................... 604/541 |
| D558,338 S | * | 12/2007 | Itoh .............................. D24/130 |
| 7,658,735 B2 | * | 2/2010 | Spehalski ..................... 604/543 |
| 2004/0230179 A1 | | 11/2004 | Shehada |
| 2005/0154373 A1 | | 7/2005 | Deutsch |

OTHER PUBLICATIONS

PCT/US2007/060156 filed Jan. 1, 2007 International Preliminary Report on Patentability and Written Opinion dated Aug. 16, 2007.
PCT/US2007/060156 filed Jan. 1, 2007 International Search Report dated Aug. 16, 2007.

\* cited by examiner

DRAINS FOR USE IN MEDICAL APPLICATIONS AND METHODS OF USING THE SAME

PRIORITY

This application is a U.S. national stage application under 35 USC § 371 of International Application No. PCT/US07/60156, filed Jan. 5, 2007, claiming priority to U.S. Provisional Application No. 60/743,103, filed Jan. 6, 2006, each of which is incorporated by reference in its entirety into this application.

TECHNICAL FIELD

The present invention is directed to drains for use in medical applications and methods of using such drains. More particularly, the present invention is directed to drains configured to be inserted into a body cavity to drain a fluid from a region of the cavity and methods of removing fluid from a region of a body cavity.

BACKGROUND

Some conventional drain tubes, such as Blake Drains, have a central lumen at a proximal end of the drain, i.e., the end nearest the user. The central lumen does not extend to the distal end of the drain. In addition, Blake Drains contain four channels for drainage of tissue and blood clots. With four channels, the cross-sectional dimension of each channel is of a small size that may inhibit drainage of tissue and blood clots.

Conventional drain tubes also lack other features that may be desirable in certain medical applications. For example, conventional drain tubes do not include mechanisms for monitoring morphological and/or physiological properties of tissue at a target site. Nor do they include a visualization mechanism for observing the target site during drainage. Conventional drains such as Blake Drains also lack a mechanism for removing plugs or debris, such as clots, that form in the drain channels.

The drains for use in medical applications and/or methods of draining a fluid from a body cavity of the present invention solve one or more of the problems set forth above.

SUMMARY OF THE INVENTION

In various aspects, the present invention is directed to a drain for use in medical applications. The drain may comprise an elongated conduit configured to be implanted in a body cavity, wherein the conduit has a proximal end and a distal end. The conduit may comprise at least one channel configured to drain fluid from the body cavity and at least one lumen extending from the proximal end to the distal end of the conduit. The lumen may be at least partially surrounded by the at least one channel and may be separated from the at least one channel by a wall. At least one hole in the wall may be configured to provide fluid communication between the lumen and the at least one channel.

In some aspects, the present invention is directed to a drain for use in medical applications. The drain may comprise an elongated conduit configured to be implanted in a body cavity, wherein the conduit has a proximal end and a distal end. The conduit may comprise at least one channel configured to drain fluid from the body cavity and at least one lumen extending from the proximal end of the conduit to the distal end. The lumen may be at least partially surrounded by the at least one channel, and a wall may separate the lumen from the at least one channel at the distal end of the conduit. The wall may comprise a porous material configured to permit diffusion of at least one fluid from the lumen to the body cavity.

According to various aspects, the present invention is directed to a method of draining a region of a body cavity. The method may comprise implanting an elongated conduit in the body cavity, wherein the conduit has a proximal end and a distal end, and supplying at least one fluid into an opening in a lumen at the proximal end of the conduit. The conduit may comprise a channel configured to drain fluid from said body cavity, and the lumen may be at least partially surrounded by the channel and separated from the channel by a wall at the distal end of the conduit. At least one fluid may be configured to diffuse through the wall and to treat a wound of the body cavity.

In accordance with some aspects, the present invention is directed to a drain for use in medical applications. The drain may comprise an elongated conduit configured to be implanted in a body cavity, wherein the conduit has a proximal end and a distal end. The conduit may comprise at least one channel configured to drain fluid from the body cavity and at least one lumen extending from the proximal end to the distal end of the conduit, wherein the lumen may be at least partially surrounded by the at least one channel. At least one sensing member may be in the lumen at a location proximal the distal end of the conduit, and the sensing member may be configured to sense at least one of a morphological and a physiological property of tissue at a desired location in the body cavity.

In accordance with various aspects, the present invention is directed to a drain for use in medical applications. The drain may comprise an elongated conduit configured to be implanted in a body cavity, wherein the conduit has a proximal end and a distal end. The conduit may comprise at least one channel configured to drain fluid from the body cavity and at least one lumen extending from the proximal end to the distal end of the conduit, wherein the lumen may be at least partially surrounded by the at least one channel. The drain may comprise a light source in the lumen at a location proximal the distal end of the conduit, wherein the light source may be configured to illuminate a desired location in the body cavity.

According to various aspects, the present invention is directed to a drain for use in medical applications. The drain may comprise an elongated conduit configured to be implanted in a body cavity, wherein the conduit has a proximal end and a distal end. The conduit may comprise at least one channel configured to drain fluid from the body cavity. The drain may comprise an elongated member slidably disposed in the channel and extending from the proximal end of the conduit to said distal end. An inflatable member may be associated with the elongated member at the distal end of the conduit, and the inflatable member may be inflatable to a size and configuration substantially complementary to a size and configuration of one of the channels.

In various aspects, the present invention is directed to a method of draining a region of a body cavity. The method may comprise implanting an elongated conduit in the body cavity, wherein the conduit may have a proximal end and a distal end, and the conduit may comprise a channel configured to drain fluid from the body cavity. The method may include slidably inserting an elongated member in the channel, wherein the elongated member may extend from the proximal end of the conduit to the distal end. The method may also comprise inflating an inflatable member associated with the elongated member at the distal end of the conduit to a size and configuration substantially complementary to a size and configuration of one of the channels, and withdrawing the elongated member and inflatable member toward the proximal end of the conduit so as to remove debris from the channel.

According to some aspects, the present invention is directed to a drain for use in medical applications. The drain may comprise an elongated conduit configured to be implanted in a body cavity, wherein the conduit has a proximal end and a distal end, and the conduit may comprise a channel configured to drain fluid from the body cavity. The drain may comprise an elongated member associated with and extending substantially the entire length of the conduit, wherein the elongated member may be configured to impart motion to the conduit. A control device may be configured to operate the elongated member so as to impart motion to the conduit.

In accordance with various aspects, the present invention is directed to a drain for use in medical applications. The drain may comprise an elongated conduit configured to be implanted in a body cavity, wherein the conduit has a proximal end, a distal end, and a longitudinal axis. The drain may include a hub portion extending axially within the conduit at the distal end, three walls extending between the hub portion and the conduit at said distal end, and at least one lumen extending from said proximal end to said distal end of the conduit. The walls may be equally spaced with respect to one another about a periphery of the hub portion, the walls may cooperate with at least one of the hub portion and the conduit to define three channels configured to drain fluid from said body cavity, and the lumen may be at least partially surrounded by at least one of the channels. Each of the three channels may have substantially the same cross-sectional area.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several exemplary embodiments of the invention and, together with the description, serve to explain the principles of the invention. In the drawings.

DETAILED DESCRIPTION

Reference will now be made in detail to embodiments of the invention, examples of which are illustrated in the accompanying drawings. Wherever possible, the same reference numbers will be used throughout the drawings to refer to the same or like parts.

Figure 1:
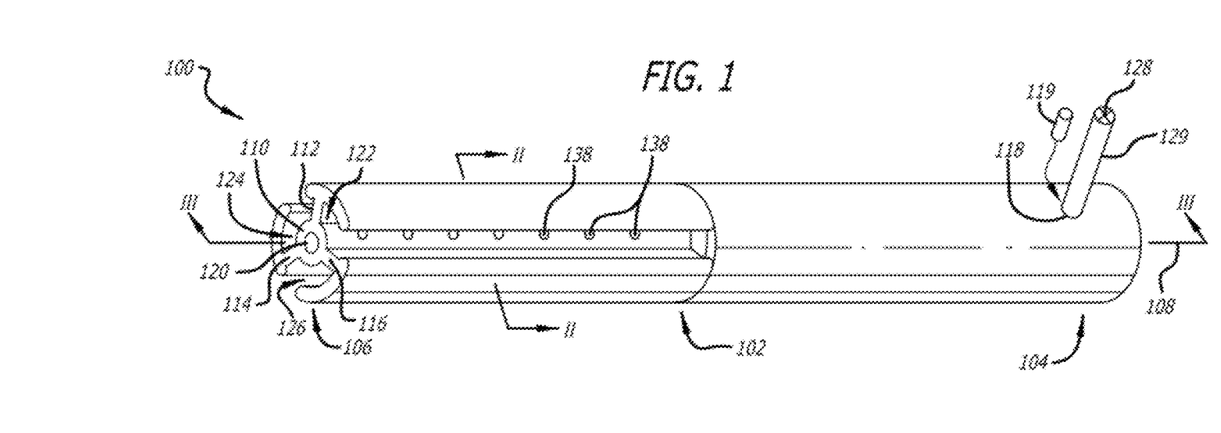
FIG. 1 is a perspective view of an exemplary drain in accordance with various aspects of the present invention.

An exemplary embodiment of a drain 100 for use in medical applications is illustrated in FIG. 1. The drain 100 may comprise an elongated conduit 102 configured to be implanted in a body cavity such as, for example, the chest cavity of a human. The conduit may have a proximal end 104, a distal end 106, and a longitudinal axis 108.

The drain 100 may include a hub portion 110 extending axially within the conduit at the distal end 106. According to various aspects, the hub portion 110 may be substantially at the center of the conduit 102, as shown in the cross-sectional view of FIG. 2.

Figure 2:
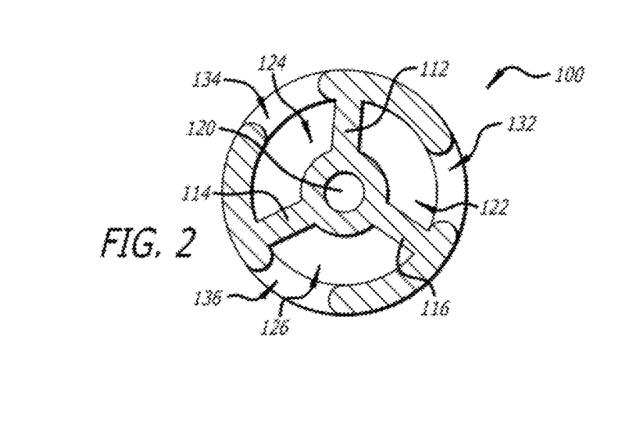
FIG. 2 is a cross-sectional view along line II-II of FIG. 1.

According to some exemplary aspects, the drain 100 may include three walls 112, 114, 116 extending between the hub portion 110 and the conduit 102 at the distal end 106. It should be appreciated that in some embodiments, the drain may include more or less than three walls. The walls 112, 114, 116 may be equally spaced with respect to one another about a periphery of the hub portion 110. According to various aspects, the walls 112, 114, 116 may cooperate with the hub portion 110 and/or the conduit 102 to define three channels 122, 124, 126 configured to drain fluid from a body cavity. In some aspects, each of the three channels 122, 124, 126 may have substantially the same cross-sectional area. As shown in FIG. 2, the three channels 122, 124, 126 comprise a significant portion of the cross-sectional area of the distal end 106 of the conduit 102. As a result, the channels 122, 124, 126 may provide a passage with a relatively large cross-sectional area so that larger clots and debris can be evacuated from the cavity. Larger channels may also result in relatively low tissue in-growth.

Figure 3:
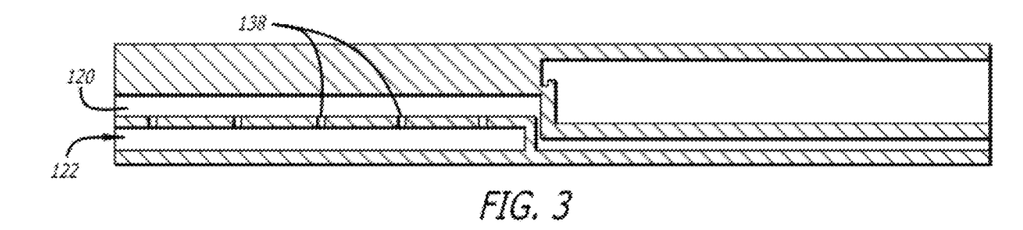
FIG. 3 is a partial cross-sectional view along line III-III of FIG. 1.

The drain 100 may include at least one lumen 120 extending from the proximal end 104 of the conduit 102 to the distal end 106. The lumen 120 may be at least partially surrounded by one or more of the channels 122, 124, 126. According to various exemplary aspects, the lumen 120 may be at the center of the distal end 106 of the conduit 102, for example, extending through the hub portion 110 of some exemplary embodiments. As shown in the cross-sectional view of FIG. 3, the lumen 120 may be in the center of the conduit 102 at the distal end 106 and toward a wall of the conduit 102 as it extends toward the proximal end 104.

The conduit 102 may include one or more slots 132, 134, 136 associated with one or more of the channels 122, 124, 126. For example, according to some aspects, the conduit 102 may comprise one slot associated with each channel. The slots 132, 134, 136 may be sized and arranged to provide fluid communication between a corresponding one of the channels 122, 124, 126 and an exterior of the conduit 102.

According to various aspects, as shown in FIG. 1, the hub portion 110 may include one or more holes 138 therethrough. The one or more holes 138 may be sized and arranged to provide fluid communication between said lumen 120 and at least one of the channels 122, 124, 126. For example, the holes 138 may be aligned with one, some, or all of the channels 122, 124, 126.

It should be appreciated that in some embodiments, the lumen 120 may be defined by a structure (not shown) separate from the hub portion 110. In such a case, the holes 138 may be through the structure defining the lumen 120 so as to provide fluid communication between the lumen 120 and one or more channels exterior to the lumen 120.

According to various aspects, in addition to or in place of the holes 138, the hub portion 110 may comprise a material that permits diffusion of a fluid from the lumen 120 through the wall of the hub portion 110 and into one or more of the channels 122, 124, 126. In some embodiments where a structure (not shown) separate from the hub portion 110 defines the lumen 120, that structure may comprise a material that permits diffusion of a fluid from the lumen 120 through the wall of the structure and into one or more of the channels 122, 124, 126. It should be appreciated that a portion or all of the hub portion 110 or structure may comprise the material that permits diffusion such that diffusion may be permitted to one or more of the channels 122, 124, 126.

In some aspects, the conduit 102 may include an opening 118, for example, a fluid port, associated with the lumen 120 at the proximal end 104 of the conduit 102. The opening may be structured and arranged to receive said at least one fluid from one or more fluid supplies (not shown). A valving member 128 may be fluidly coupled to the opening 118 via a fluid line 129. The valving member 128 may be operable, either manually or automatically, to selectively open and close so as to permit or block fluid flow to the opening 118

It should be appreciated that in some aspects, the opening 118 may be selectively opened and closed with a plug 119. The plug 119 may be structured and arranged to be removably inserted into the opening. According to some aspects, the lumen 120 may be at least partially filled with at least one fluid, and then the plug 119 may be inserted into the opening 118 to prevent the at least one fluid from flowing out of the opening 118.

Figure 4:
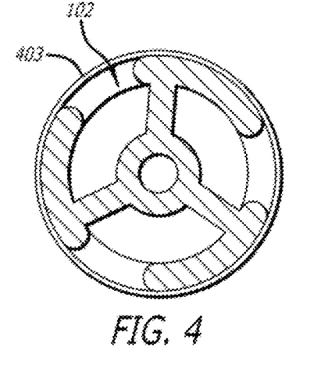
FIG. 4 is a cross-section view similar to that of FIG. 2 illustrating various aspects of the invention.

Referring to FIG. 4, in accordance with some embodiments, the conduit 102 may comprise a coating 403, for example, an anti-inflammatory, anti-infective, lubricious, and/or mucolytic coating. For example, the coating may comprise salicylic acid, acetaminophen, aloe vera, silver, chlorhexidine, polyhexamethyl biguianide, and/or NSAIDS. Additional non-limiting examples of suitable coatings can be found in U.S. Pat. Nos. 6,329,488, 6,596,401, 6,716,895 and 6,949,598, the disclosures of which are incorporated herein by reference in their entirety.

Figure 5:
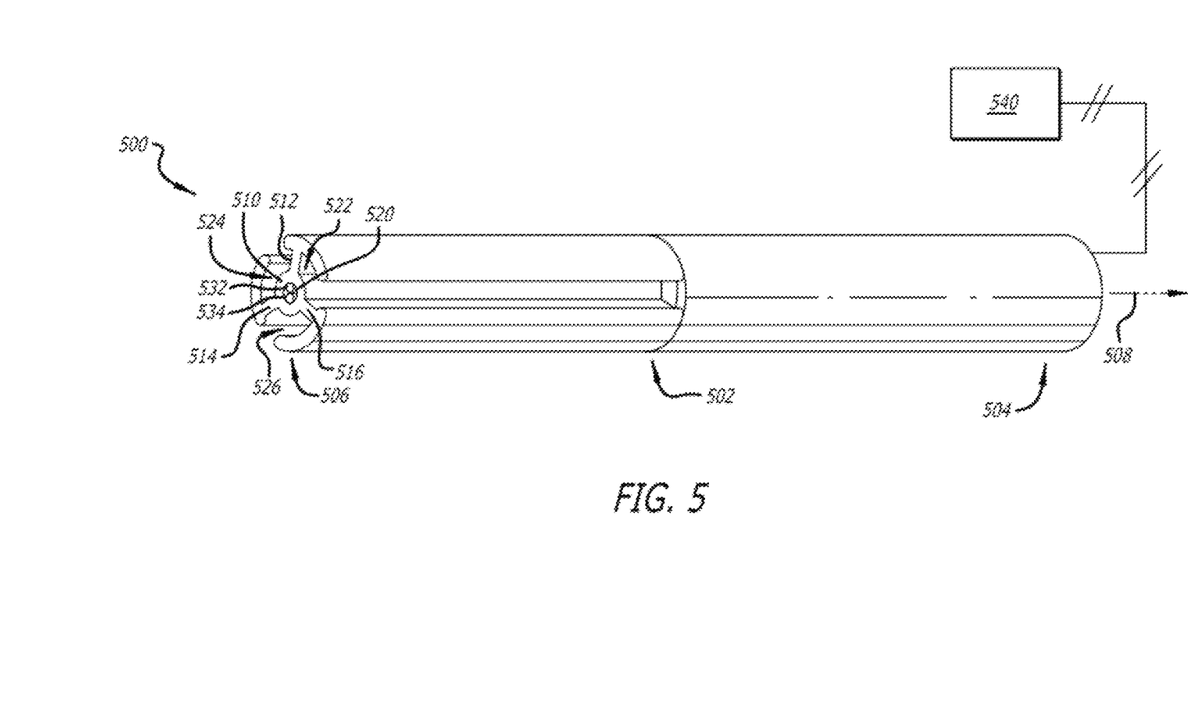
FIG. 5 is a perspective view of an exemplary drain in accordance with various aspects of the present invention.

Referring now to FIG. 5, an exemplary drain 500 for use in medical applications is illustrated. The drain 500 may comprise an elongated conduit 502 configured to be implanted in a body cavity such as, for example, the chest cavity of a human. The conduit may have a proximal end 504, a distal end 506, and a longitudinal axis 508.

The drain 500 may include a hub portion 510 extending axially within the conduit at the distal end 506. The hub portion 510 may define a lumen 520 extending from the proximal end 504 of the conduit 502 to the distal end 506. According to various aspects, the hub portion 510 may be substantially at the center of the conduit 502. It should be appreciated that in some aspects, the hub portion 510 may be disposed toward a wall of the conduit 502. It should further be appreciated that in some embodiments, the lumen 520 may be defined by a structure (not shown) separate from the hub portion 510.

According to some exemplary aspects, the drain 500 may include a plurality of walls 512, 514, 516 extending between the hub portion 510 and the conduit 502 at the distal end 506. It should be appreciated that in some embodiments, the drain may include more or less than the three walls shown in FIG. 5. According to various aspects, the walls 512, 514, 516 may cooperate with the hub portion 510 and/or the conduit 502 to define a plurality of channels 522, 524, 526 configured to drain fluid from a body cavity.

In accordance with some exemplary aspects, the drain 500 may comprise one or more sensing members 532 in the lumen 520 at a location proximal the distal end 506 of the conduit 502. The sensing member 532 may be configured to sense, for example, one or more morphological properties and/or one or more physiological properties of tissue at a desired location in a body cavity. For example, the sensing member 532 may be configured to sense parameters that can be used to determine temperature, pressure, tissue $O_2$ and/or pH. It should be appreciated that the sensing member 532 may be configured to sense other parameters, as would be understood by persons skilled in the art.

The sensing member 532 may be electrically connected to a controller 540 via, for example, an electrical wire or a wireless connection. The controller 540 may be configured to receive, process and/or interpret signals received from the sensing member 532. The controller 540 may be configured to output information regarding the morphological and/or physiological properties in a form understandable by a user.

According to various exemplary aspects, the drain 500 may comprise a light source 534 in the lumen 520 at a location proximal the distal end 506 of the conduit 502. The light source 534, for example, a fiber optic light source, may be configured to illuminate a desired location in a body cavity. In some aspects, the light source 534 may be electrically connected to the controller 540, which in turn may be configured to controllably operate the light source 534. It should be appreciated that one or more sensing members 532 and the light source 534 may co-exist in some embodiments, while other embodiments may include one or more sensing members 532 or a light source 534. According to some aspects, the sensing members 532 may sense vacuum effects or may comprise one or more transducers, such as pressure-sensing and/or pH sensing transducers, temperature thermistors, and/or a visualization mechanism such as, for example, a still camera or a video camera. The camera may assist with assessment of wound healing and/or cavity drainage, and may comprise disposable optics. According to some aspects, the transducers may comprise ultrasound transducers.

Figure 6:
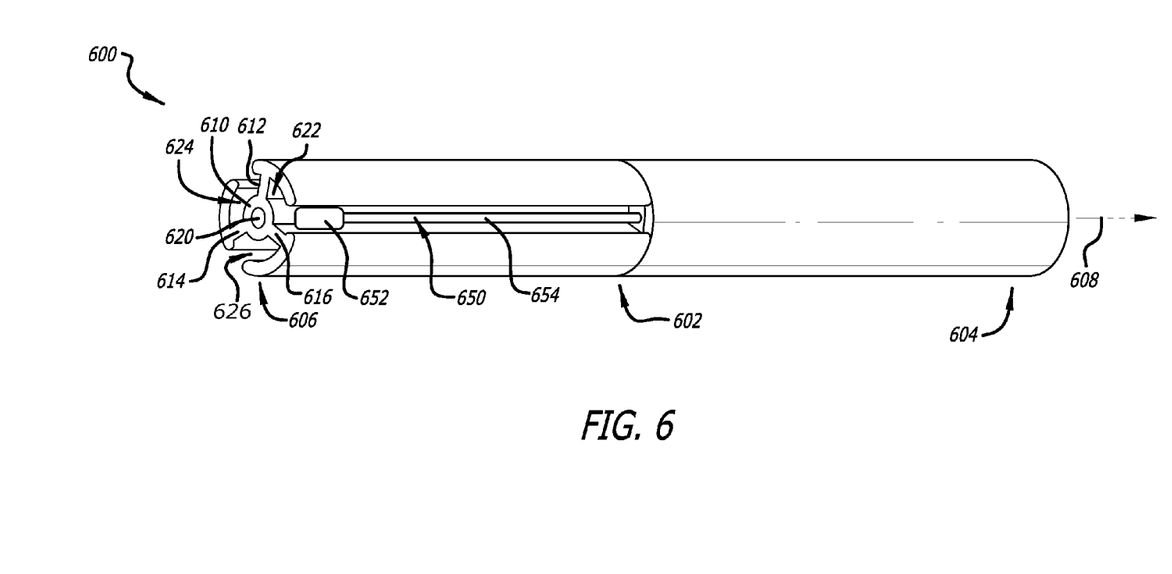
FIG. 6 is a perspective view of an exemplary drain in accordance with various aspects of the present invention.

Referring now to FIG. 6, an exemplary drain 600 for use in medical applications is illustrated. The drain 600 may comprise an elongated conduit 602 configured to be implanted in a body cavity such as, for example, the chest cavity of a human. The conduit may have a proximal end 604, a distal end 606, and a longitudinal axis 608.

The drain 600 may include a hub portion 610 extending axially within the conduit at the distal end 606. The hub portion 610 may define a lumen 620 extending from the proximal end 604 of the conduit 602 to the distal end 606. According to various aspects, the hub portion 610 may be substantially at the center of the conduit 602. It should be appreciated that is some aspects, the hub portion 610 may be disposed toward a wall of the conduit 602. It should further be appreciated that in some embodiments, the lumen 620 may be defined by a structure (not shown) separate from the hub portion 610.

According to some exemplary aspects, the drain 600 may include a plurality of walls 612, 614, 616 extending between the hub portion 610 and the conduit 602 at the distal end 606. It should be appreciated that in some embodiments, the drain may include more or less than the three walls shown in FIG. 6. According to various aspects, the walls 612, 614, 616 may cooperate with the hub portion 610 and/or the conduit 602 to define a plurality of channels 622, 624, 626 configured to drain fluid from a body cavity.

The drain 600 may comprise an elongated member 650 slidably disposed in one of the channels 622, 624, 626. The elongated member 650 may extend from the proximal end 604 to the distal end 606 of the conduit 602. An inflatable member 652 may be associated with the elongated member 650 toward the distal end 606 of the conduit 602. The inflatable member 652 may be inflatable, for example, by providing inflation air to the inflatable member 652 via, for example, a lumen 654 extending through the elongated member 650.

As shown in FIG. 6, the inflatable member 652 may be inflatable to a size and configuration substantially complementary to the size and configuration of the channel 622. Thus, once the inflatable member 652 is substantially inflated, the inflatable member 652 can be urged in a direction toward the proximal end 604 of the conduit 602, thereby removing debris from the channel 622, for example, debris that may be clogging the channel.

Figure 7:
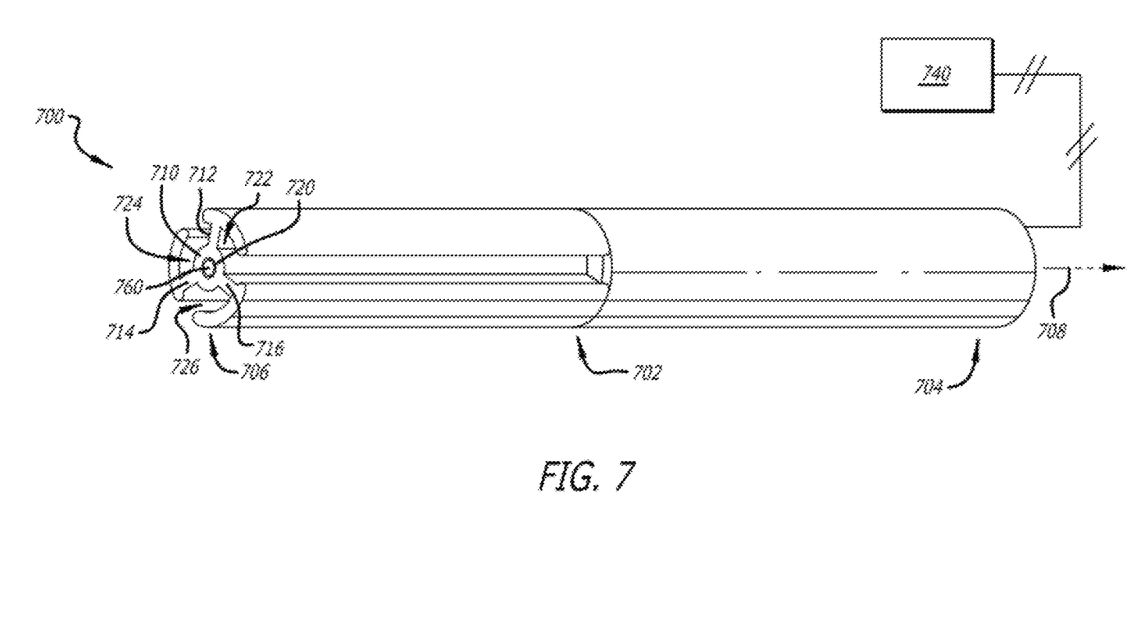
FIG. 7 is a perspective view of an exemplary drain in accordance with various aspects of the present invention.

Referring now to FIG. 7, an exemplary drain 700 for use in medical applications is illustrated. The drain 700 may comprise an elongated conduit 702 configured to be implanted in a body cavity such as, for example, the chest cavity of a human. The conduit may have a proximal end 704, a distal end 706, and a longitudinal axis 708.

The drain 700 may include a hub portion 710 extending axially within the conduit at the distal end 706. The hub portion 710 may define a lumen 720 extending from the proximal end 704 of the conduit 702 to the distal end 706. According to various aspects, the hub portion 710 may be substantially at the center of the conduit 702. It should be appreciated that is some aspects, the hub portion 710 may be disposed toward a wall of the conduit 702. It should further be appreciated that in some embodiments, the lumen 720 may be defined by a structure (not shown separate from the hub portion 710.

According to some exemplary aspects, the drain 700 may include a plurality of walls 712, 714, 716 extending between the hub portion 710 and the conduit 702 at the distal end 706. It should be appreciated that in some embodiments, the drain may include more or less than the three walls shown in FIG. 6. According to various aspects, the walls 712, 714, 716 may cooperate with the hub portion 710 and/or the conduit 702 to define a plurality of channels 722, 724, 726 configured to drain fluid from a body cavity.

The drain 700 may comprise an elongated member 760 associated with and extending substantially the entire length of the conduit 702. As shown in FIG. 7, according to some aspects, the elongated member 760 may be in the lumen 720. According to various aspects, the elongated member 760 may be in one of the channels 722, 724, 726, or the member 760 may be embedded in the hub 710, the walls 712, 714, 716, or the conduit 702, or the member 760 may be on an exterior of the conduit. The elongated member 760 may be structured and arranged to impart motion (e.g., translational and/or rotational) to the conduit 702 as would be understood by a person skilled in the art. The elongated member 760 may be electrically connected to a control device 740 configured to operate the elongated member 760 so as to impart motion to the conduit as would be under stood by a person skilled in the art. Thus, the conduit may be repositioned upon insertion or after initial placement. In accordance with various aspects, the control device 740 may comprise one or more dials, one or more joysticks, or the like for accommodating user inputs to controllably move and/or operate the elongated member 760 and/or the drain 700.

It should be appreciated that one or more of the aforementioned conduits 502, 602, 702 may comprise a coating, for example, an anti-inflammatory, anti-infective, lubricious, and/or mucolytic coating. For example, the coating may comprise salicylic acid, acetaminophen, aloe vera, silver, chlorhexidine, polyhexamethyl biguianide, and/or NSAIDS.

It should also be appreciated that one or more of the aforementioned exemplary drains 100, 500, 600, 700 may comprise one or more elements comprising a shape memory alloy such as, for example, nitinol. The use of a shape memory alloy may allow the drain 100, 500, 600, 700 to be configured for a desired use, altered to a different configuration during a portion of procedure, and allowed to re-assume its original configuration. Exemplary shape memory alloys, such as nitinol, and their uses are well-known to persons skilled in the art.

It should be appreciated that one or more of the aforementioned drains 500, 600, 700 may comprise a conduit with an opening similar to the opening 118 described above in connection with FIG. 1. In addition, any one or more of the exemplary aspects discussed in connected with one or more of the aforementioned exemplary drains 100, 500, 600, 700 may be used in combination with one other as would be understood by a person skilled in the art.

It should also be appreciated that one or more of the aforementioned drains 100, 500, 600, 700 may comprise a port (not shown) associated with the distal end of the conduit. The port may be configured to removably receive a trocar such that the trocar has a distal end extending from the distal end of the conduit.

It should be appreciated that the aforementioned exemplary drains 100, 500, 600, 700 may be used in various medical applications. For example, one exemplary method of draining a region of a body cavity may comprise implanting an elongated conduit 102, 502, 602, 702 in the body cavity, and supplying at least one fluid into an opening 118 into a lumen 120, 520, 620, 720 at a proximal end 104, 504, 604, 704 of the conduit 102, 502, 602, 702. The lumen 120, 520, 620, 720 may be configured to permit diffusion of at least one fluid through a wall of the lumen to treat a wound of the body cavity. A valving member or plug may be used to prevent the fluid from flowing out of the opening 118.

According to various aspects, an exemplary method of draining a region of a body cavity may comprise implanting an elongated conduit 602 in the body cavity and slidably inserting an elongated member 650 in a channel 622 defined at least in part by the conduit 602. An inflatable member associated with the elongated member at said distal end of the conduit may then be inflated to a size and configuration substantially complementary to a size and configuration of the channel 622. The inflated member 652 may be withdrawn in a direction toward the proximal end 604 of the conduit 602 so as to remove debris from the channel 622.

It is noted that, as used in this specification and the appended claims, the singular forms "a," "an," and "the," include plural referents unless expressly and unequivocally limited to one referent. Thus, for example, reference to "a channel" includes two or more different channels. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made in the drain and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A drain for use in medical applications, comprising:
an elongated conduit configured to be implanted in a body cavity, the conduit having a longitudinal axis, a proximal end, and a distal end, the conduit comprising
at least one channel configured to drain fluid from said body cavity,
at least one slot associated with said at least one channel, providing fluid communication between said at least one channel and an exterior of the conduit, at least one lumen extending from said proximal end to said distal end of the conduit, said lumen positioned centrally along a distal section of the conduit and positioned toward a wall of the conduit along a proximal section of the conduit, said lumen being at least partially surrounded by said at least one channel, and a wall separating said lumen from said at least one channel at said distal end of the conduit, the wall comprising a porous material configured to permit diffusion of at least one fluid from said lumen to said body cavity.

2. The drain of claim 1, further comprising an opening associated with the lumen at said proximal end of the conduit, the opening being configured to receive said at least one fluid.

3. The drain of claim 2, further comprising a valving member configured to selectively open and close said opening.

4. The drain of claim 2, further comprising a plug insertable into said opening to prevent fluid from flowing out of said opening.

* * * * *